(12) United States Patent
Lin (10) Patent No.: US 9,273,822 B2
(45) Date of Patent: Mar. 1, 2016

(54) SUPPORT APPARATUS

(71) Applicant: WISTRON CORP., New Taipei (TW)

(72) Inventor: Heng-Yu Lin, New Taipei (TW)

(73) Assignee: WISTRON CORP., New Taipei (TW)

( * ) Notice: Subject to any disclaimer, the term of this patent is extended or adjusted under 35 U.S.C. 154(b) by 363 days.

(21) Appl. No.: 13/887,286

(22) Filed: May 4, 2013

(65) Prior Publication Data

US 2014/0054251 A1 Feb. 27, 2014

(30) Foreign Application Priority Data

Aug. 24, 2012 (TW) .............................. 101216349 U (51) Int. Cl.
*F16M 13/00* (2006.01)
*F16M 11/04* (2006.01)

(52) U.S. Cl.
CPC ............. *F16M 13/00* (2013.01); *F16M 11/046* (2013.01)

(58) Field of Classification Search
CPC ........... G01M 7/08; G01N 3/30; G01N 3/303; G01N 2203/001; G01N 2203/0033; F16M 13/00; F16M 11/046
USPC .................... 73/12.01, 12.04, 12.06, 865.3
See application file for complete search history.

(56) References Cited

U.S. PATENT DOCUMENTS

| | | | | |
|---|---|---|---|---|
| 1,059,464 A * | 4/1913 | Hine ..................... | A47B 57/265 | 108/107 |
| 2,767,573 A * | 10/1956 | De Vost Valmore ... | G01N 3/303 | 73/12.06 |
| 3,652,048 A * | 3/1972 | Hartman .............. | A47B 57/565 | 108/108 |
| 3,879,906 A * | 4/1975 | Hollenberg ............... | F16B 9/02 | 248/188 |
| 5,279,231 A * | 1/1994 | Kolvites ............... | A47B 57/545 | 108/107 |
| 5,279,232 A * | 1/1994 | Gollick ................... | F16B 12/24 | 108/109 |
| 5,393,135 A * | 2/1995 | Tisbo ................. | G11B 33/0433 | 206/309 |
| 5,595,127 A * | 1/1997 | Eustace ................ | A47B 47/025 | 108/109 |
| 6,171,400 B1 * | 1/2001 | Wingo .............. | H01L 21/67309 | 118/500 |
| 6,357,604 B1 * | 3/2002 | Wingo .............. | H01L 21/67309 | 118/500 |
| 6,378,710 B1 * | 4/2002 | Grueneberg ............ | A47F 5/116 | 211/132.1 |
| 6,811,040 B2 * | 11/2004 | Payne ............... | H01L 21/67303 | 206/832 |

(Continued)

FOREIGN PATENT DOCUMENTS

TW    M255682    2/2004
TW    M301584    12/2006

*Primary Examiner* — Patrick Hawn
(74) *Attorney, Agent, or Firm* — Li & Cai Intellectual Property (USA) Office (57) ABSTRACT

A height adjustable support apparatus suitable for notebook computer drop test is provided. The support apparatus includes a frame unit and a plank unit. The frame unit has a plurality of mortises vertically incrementally arranged at a lateral adjoining edge of a first lateral surface and a second lateral surface thereof. The plank unit includes a support portion and a tenon extending from the support portion configured to be insertable into one of the mortises through the first lateral surface. The support portion is configured to protrude from the second lateral surface upon insertion. The support portion incorporates a biased height arrangement that provides higher degree of height adjustment variation through different insertion orientations, and allows two plank units to be arranged in a vertically adjacent configuration to structurally abut against each other, thereby enhancing structural integrity of the support portion and increasing the load carrying capacity.

13 Claims, 6 Drawing Sheets

(56) References Cited

U.S. PATENT DOCUMENTS

| | | | | |
|---|---|---|---|---|
| 7,086,633 B2 * | 8/2006 | Welch | ................ | F16B 12/2009 108/147.13 |
| 7,596,985 B2 * | 10/2009 | Ido | ................ | G01N 3/303 73/11.01 |
| 8,047,379 B2 * | 11/2011 | Chiu | ................ | H01L 21/67383 206/710 |
| 8,387,799 B2 * | 3/2013 | Chiu | ................ | H01L 21/67383 206/710 |
| 8,413,814 B2 * | 4/2013 | Ku | ................ | H01L 21/67383 206/710 |
| 2003/0102788 A1 * | 6/2003 | Dallman | ................ | F25D 25/024 312/408 |
| 2005/0205502 A1 * | 9/2005 | Brown | ................ | H01L 21/67309 211/41.18 |
| 2007/0006803 A1 * | 1/2007 | Cadwell | ................ | C30B 25/12 117/200 |
| 2010/0051503 A1 * | 3/2010 | Chiu | ................ | H01L 21/67383 206/711 |

* cited by examiner

SUPPORT APPARATUS

FIELD OF THE INVENTION

The instant disclosure relates to a height adjustable support apparatus, and more specifically, to a height adjustable platform suitable for notebook drop-test, which utilizes a tenoned support member and a mortised support frame that enables convenient height adjustment.

BACKGROUND

To ensure reliability and quality, notebook computers are often subjected to rigorous testing. One of the most commonly deployed tests is the drop test, in which a notebook computer is repeatedly dropped (on its side) from a platform, starting from a lower position off the ground to an incrementally increased position if the notebook survives a previous altitude (e.g. at an incremental increase of 1 centimeter). The test is often carried out repeatedly until the notebook survives the drop test from an acceptable altitude.

Conventional low-cost drop test platforms lack the flexibility in height adjustment. As such, a successful conduction of drop test often requires several test platforms of different heights, which causes great practical inconvenience.

SUMMARY

It is an objective of the instant disclosure to provide a height adjustable support apparatus, where the height of the support surface thereof can be easily adjusted and securely configured to support a wide range of weight loading.

The instant disclosure also provides a height adjustable support apparatus comprises a main body and a pair of symmetrically mirroring support frame structures respectively arranged on the opposite lateral sides of the main body capable of providing balanced support for a test subject.

The instant disclosure further provides a plank unit insertable into the abovementioned support frame structure to generate a flexible range of height/altitude variations suitable for the conduction of notebook computer drop tests.

A first embodiment of the instant disclosure provides a height adjustable support apparatus that comprises a frame unit and a plank unit. The frame unit has a plurality of mortises vertically incrementally arranged at a lateral adjoining edge of a first lateral surface and a second lateral surface with substantially equal separation there-between, and are disposed between a top frame surface and a bottom frame surface thereof. The mortises define a comb-like structure on the first lateral surface. The plank unit includes a support portion and a tenon extending from the support portion configured to be insertable into one of the mortises through the first lateral surface. The support portion is configured to protrude from the second lateral surface upon insertion.

In one embodiment of the instant disclosure, the thickness of the support portion of the plank unit is greater than the width of the second side opening of the mortise defined on the second lateral surface, and is configured to incorporate a unsymmetrical/biased height arrangement, so that upon insertion into a first mortise of the frame unit, an upper support surface of the support portion is substantially flush with an upper boundary of the first mortise, while a bottom support surface thereof is substantially flush with an upper boundary of a second mortise immediately below the first mortise.

In one embodiment of the instant disclosure, the mortises are configured to be vertically symmetrical. The tenon of the plank unit is correspondingly shaped to allow structural adaptation into the mortises in either an upright orientation or a reversed orientation.

In one embodiment of the instant disclosure, the first side opening of the mortise defined on the first lateral surface is tapered, with a first (outer) end thereof proximate the second lateral surface being narrower than a second (inner) end thereof opposite to the first end.

In one embodiment of the instant disclosure, the second side openings of the mortises defined on the second lateral surface have substantially identical opening widths, and the separation distance between each pair of adjacent second side openings substantially equals to the opening width.

In one embodiment of the instant disclosure, the support surfaces of the support portion resemble a triangular shape or the shape of a circular segment.

In one embodiment of the instant disclosure, the width of each mortise is defined by the width of the second side openings, and is substantially identical to the opening width. The thickness of the support portion of the plank unit is twice the width of the mortise.

In one embodiment of the instant disclosure, when two identical plank units are arranged in a vertically adjacent configuration, the upper support surface of the second support portion abuts against the bottom support surface of the first support portion (122) from below, thereby enhancing structural integrity of the support portions and thus increasing load carrying capacity of the plank unit.

A second embodiment of the instant disclosure provides a height adjustable support apparatus that comprises a main body and a pair of symmetrically mirroring support frame structures respectively arranged on the opposite lateral sides of the main body. Each of the support frame structures includes a frame body that shares similar structural design with first embodiment. The symmetrically mirroring arrangement of the support frame structures enables the support apparatus to provide balanced support for a test subject.

Another aspect of the instant disclosure provides a plank unit that comprises a support portion having a vertically unsymmetrical/biased upper and lower support surfaces configuration. The thickness of the support portion is not only thicker than the width of the mortise but also biasedly arranged. On the other hand, the vertically symmetrical configuration of the mortise allows the plank unit to be inserted in either an upright or a reversed orientation. Thus, upon insertion into a first mortise of the frame unit, the upper support surface of the support portion is substantially flush with an upper boundary of the first mortise, while a bottom support surface thereof is substantially flush with an upper boundary of a second mortise immediately below the first mortise. The unsymmetrical layout of the plank unit enables the provision of different support surface altitudes depending on the insertion orientation of the plank unit.

Accordingly, the instant disclosure provides a height adjustable support apparatus, where the height of the support surface thereof can be easily adjusted and securely configured to support a wide range of weight loading, thereby providing higher degree of operating convenience and practicality, and eliminating the inconvenient need for having multiple drop-test carriers of different heights.

These and other features and advantages of the present invention will be described in, or will become apparent to those of ordinary skill in the art in view of, the following detailed description of the exemplary embodiments of the present invention.

BRIEF DESCRIPTION OF THE DRAWINGS

The novel features believed characteristic of the invention are set forth in the appended claims. the invention itself, however, as well as a preferred mode of use, further objectives and advantages thereof, will best be understood by reference to the following detailed description of an illustrative embodiments when read in conjunction with the accompanying drawings, wherein:

DETAILED DESCRIPTION

The instant disclosure will be described more specifically with reference to the following embodiments. It is to be noted that the following descriptions of preferred embodiments are provided herein for purpose of illustration and description. It is not intended to be exhaustive or limiting to the precise form disclosed.

[First Embodiment]

Figure 1:
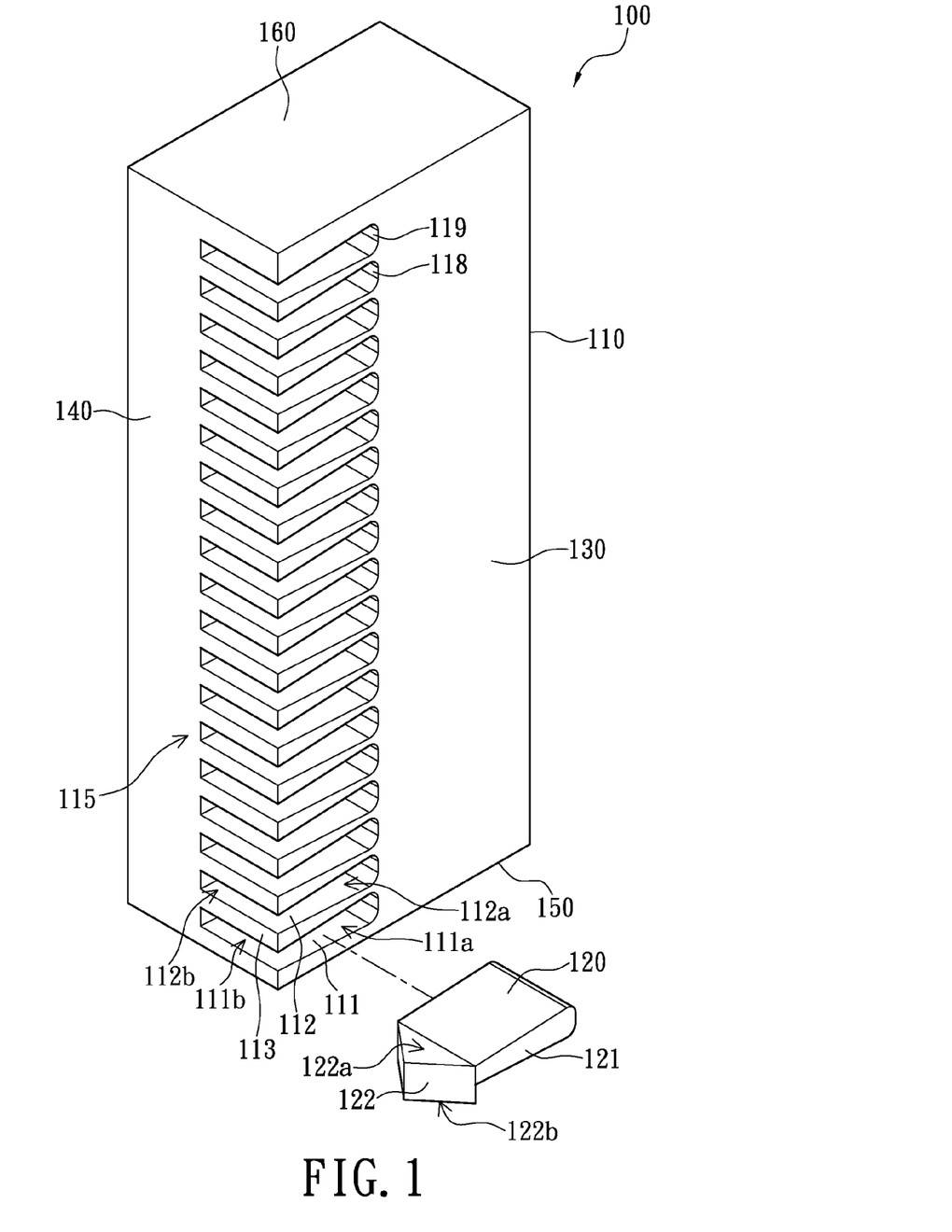
FIG. 1 illustrates a height adjustable support apparatus in accordance with a first embodiment of the instant disclosure.

Please refer to FIG. 1, which shows an isometric view of a height adjustable support apparatus in accordance with a first embodiment of the instant disclosure. The height adjustable support apparatus 100 comprises a frame unit 100 and at least one plank unit 120. The plank units 120 are configured to be insertable into any one of the mortises/slots (e.g. 111~119) of the frame unit 110 to form the complete support platform 100. The mortises 111~119 are arranged at the adjoining edge of two lateral surfaces of the frame unit 110 and configured to enable insertion of the plank unit 120 therein. The plank unit 120 comprises a protruding support portion 122 having a upper support surface 122a and a lower support surface 122b configured to generate two different height variations depending on the insertion orientation of the plank unit 120 (i.e., when the plank unit 120 is inserted with the upper support surface 122a facing up, or when it is inserted with the lower support surface 122b facing up). In addition, the different height arrangement of the upper and lower support surfaces (122a/b) allows two plank units 120 to structurally abut against each other upon insertion into the frame unit 110 when arranged in a vertically adjacent configuration, thereby enhancing structural integrity of the support portion and increasing load carrying capacity of the plank unit.

Figure 2:
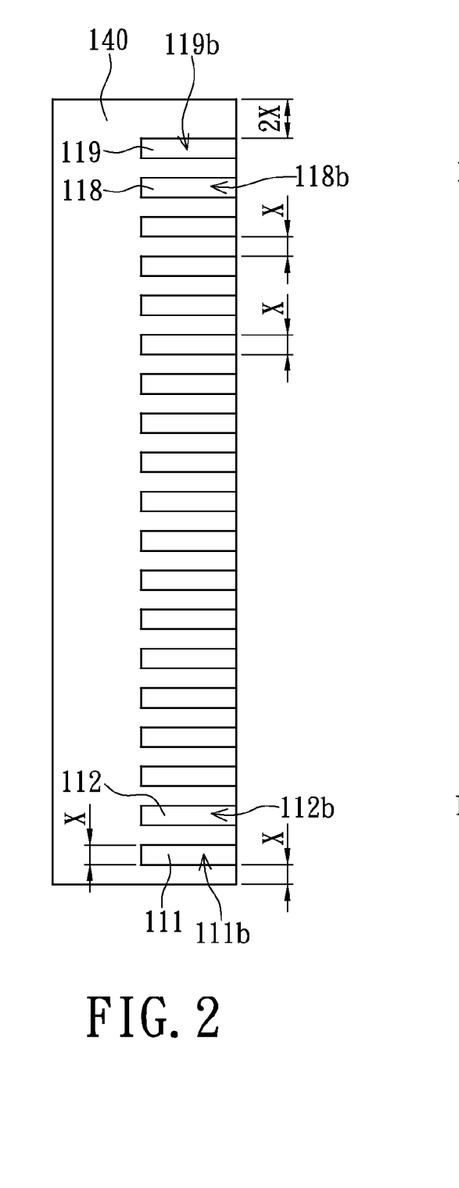
FIG. 2 illustrates side view of a height adjustable support apparatus in accordance with the first embodiment of the instant disclosure observed from the second side 140.
Figure 3:
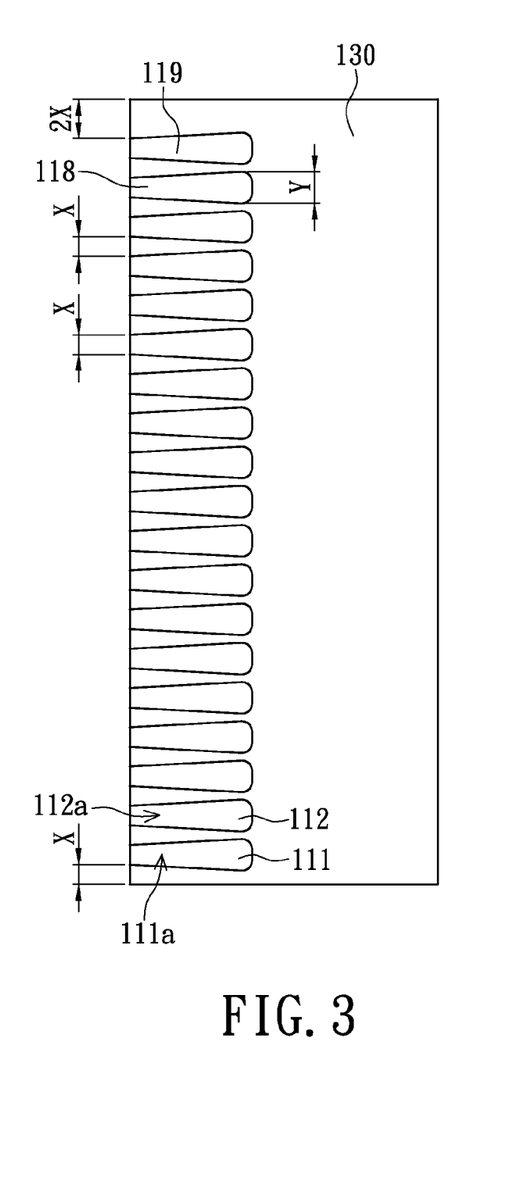
FIG. 3 illustrates side view of a height adjustable support apparatus in accordance with the first embodiment of the instant disclosure observed from the second side 130.

Please concurrently refer to FIGS. 1-3 for more detailed illustrations of the structural design/arrangement of the exemplary support apparatus 100. Specifically, the frame unit 110 has a top frame surface 160, and bottom frame surface 150, and a plurality of lateral surfaces (including a first lateral surface 130 and a second lateral surface 140 immediately adjacent thereto). Preferably, the frame unit 110 is capable of being arranged in both an upright orientation (with the frame unit standing on the bottom frame surface 150, as shown in FIG. 1) and a reversed orientation (with the frame unit standing on the top frame surface 160). A plurality of mortises (e.g. 111~119) are vertically arranged at the adjoining edge of the first and second lateral surfaces (130, 140). Specifically, the plurality of mortises 111~119 are vertically arranged with substantially equal separation at the adjoining edge of the first and the second lateral surfaces, forming a comb-like structure 115 (when viewing from a side angle, as shown in FIGS. 2 and 3). Each mortis (111) constitutes a first side opening (111a) accessible from the first lateral surface (130) and a second side opening (111b) accessible from the second lateral surface (140).

Each two neighboring mortis (e.g. 111, 112) are separated by a dividing member 113 (i.e. the teeth of the comb). The thickness (height) of the dividing member 113 is defined to be the separation distance between the mortises 111 and 112 on the second lateral surface, i.e., the separation distance between second side openings 111b and 112b. Preferably, the plurality of mortises 111~119 are incrementally arranged with substantially equal separation between the top frame surface 160 and the bottom frame surface 150. In the instant embodiment, the separation distances between each two adjacent mortises (e.g. 111, 112) are substantially equal. In other words, the dividing members 113 of the comb structure 115 are of substantially equal thickness (height). It is worth noting that, the height of the dividing member 113, and the separation between mortise 111 and mortise 112, are defined by the thickness of the dividing member 113 on the second lateral surface 140 and the width of the second side opening 111b, respectively.

In more quantitative terms, the separation distance between the neighboring mortises 111 and 112 (i.e., the height of the dividing member 113) is defined by the separation distance between the second side openings 111b and 112b on the second lateral surface 140. In the instant embodiment, we define the separation distance between the two neighboring mortises 111 and 112 to be X, where X is a positive number. The separation distance X is maintained between each pair of the immediately adjacent mortises, such as mortises 118b and 119b. Preferably, the width of each individual mortise (e.g. 111, 112), which is defined by the width of the second side openings (e.g. 111b, 112b), is also substantially equal. In the instant embodiment, the width (or "height") of the mortise 111/112 on the second lateral surface 140 is also X. In other words, on the second lateral surface 140, the separation distance between each pair of neighboring second side openings (e.g. 111b and 112b) equals the width of the respective second side openings (e.g., the width of 111b or 112b, which are substantially identical). Furthermore, in the instant embodiment, the distance from the top frame surface 160 to the highest (nearest) mortise (i.e. mortise 119) is arranged to be 2x, while the distance from the bottom frame surface 150 to the lowest (nearest) mortise (i.e. mortise 111) is arranged to be X (please refer to FIGS. 2 and 3 for a clearer illustration). Such a design configuration enables the frame unit 110 to provide two different initial heights: the first initial height is provided when the frame unit 110 is disposed in the upright orientation (when standing on the bottom frame surface 150, in which the initial height is X); the second initial is provided when the frame unit 110 is disposed in the reversed orientation (when standing on the top frame surface 160, in which the initial height is 2x). In the instant embodiment, the value of X is set to be 0.5 centimeter. However, the value of separation increment X can be selected depending on practical needs or other specific requirements.

With the abovementioned design features, the frame unit 110 can provide more altitude setting varieties by merely changing the disposition orientation thereof (i.e. when being arranged upright or in the reversed orientation). Of course, the detail arrangements, such as the width of the opening, the separation distance, as well as the separation between the highest/lowest mortis to the top/bottom frame surface, can be selected basing on specific requirements or practical needs, and shall not be limited to the particular conditions set forth in this exemplary embodiment, such as that shown in FIGS. 1-3. For example, the width of the mortis 111 can be set to 2x, while the distance between the highest mortis (i.e. 119) to the top frame surface 160 can be set to 3x or 4x, and shall not be limited to the examples provided by the instant exemplary embodiment.

Each of the mortis (e.g. 111-119) constitutes a corresponding first side opening (e.g. 111a-119a) accessible from the first lateral surface (130) and a second side opening (e.g. 111b-119b) accessible from the second lateral surface (140), as shown in FIGS. 2 and 3. Moreover, the first side openings (e.g. 111a-119a) have a tapered configuration. Please refer specifically to FIG. 3, using the orientation provided by the figure. In a side view of the first lateral surface 130, the left end of the first side opening 111a (i.e. the end proximate the second later surface 130, which has a width X) is configured to be narrower than the right end (which has a width Y) thereof. On the other hand, as previously mentioned, the mortise opening on the second lateral surface 140 (i.e. the second side openings such as 111b) maintains a fixed opening width (as shown in FIG. 2). Thus, the abovementioned configuration allows the plank unit 120 to only be inserted into the mortise of the frame unit 110 through the tapered first side openings (e.g. 111a-119a), with the support portion 122 protruding from the second lateral surface 140 of the frame unit 110 for supporting/carrying a load, such as a notebook computer waiting to be "pushed off the plank" during a drop test. With this structural arrangement, once inserted into a mortise of the frame unit 110 through a first side opening (e.g. 111a), the plank unit 120 can be retained in the mortise securely and will not easily fall out through the second side opening (e.g. 111b, since the load carrying support portion 122 is protrudingly arranged from the second lateral surface 140). Preferably, the mortises (111-119) are configured to be vertically symmetrical, and a tenon 121 (will be discussed in more detail in the following paragraph) of the plank unit 120 is correspondingly shaped to allow structural adaptation into the mortises, thereby allowing the plank unit 120 to be inserted into the mortise in a face-up orientation (with the upper support surface 122a facing up), or in a face-down orientation (with the lower support surface 122b facing up). Due to the unsymmetrically height arrangement of the support portion 122, the choice between the face-up and the face-down orientations allows the plank unit 120 to offer a higher degree of height variation selectivity. The rest of the mortises 112, 118, 119 share same structural design features as recited above, thus will not be repetitively discussed.

Figure 4:
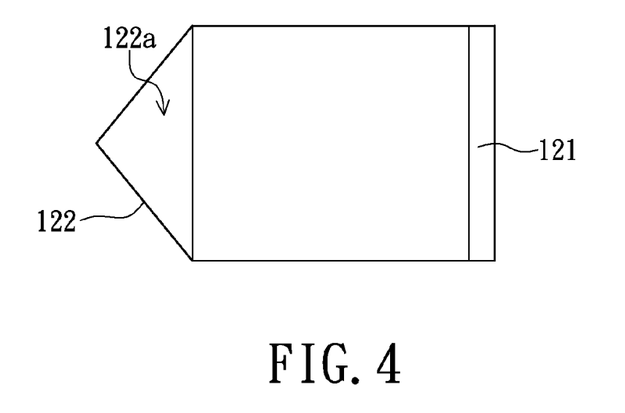
FIG. 4 illustrates a top view of a plank unit 120 in accordance with the first embodiment of the instant disclosure.
Figure 5:
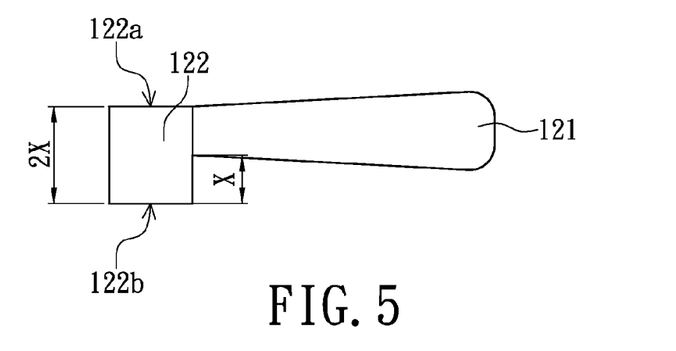
FIG. 5 illustrates a side view of a plank unit 120 in accordance with the first embodiment of the instant disclosure.

Please refer to FIGS. 4 and 5, which show a top view and a side view of the plank unit 120 in accordance with the first embodiment, respectively. The plank unit 120 comprises a support portion 122 and a tenon portion 121 extending therefrom. As previously mentioned, the structural configuration of the tenon 121 is correspondingly shaped allow insertion thereof into the mortise (e.g. 111, 112) through the tapered first side openings (e.g. 111a, 112a) from the first lateral surface 130. Take mortise 111 for instance. The tenon 121 of the plank unit 120 is shaped to be insertable into the mortis 111 through the first side opening 111a, while the support portion 122 thereof extends from the second lateral surface 140 of the frame unit 110.

Figure 6:
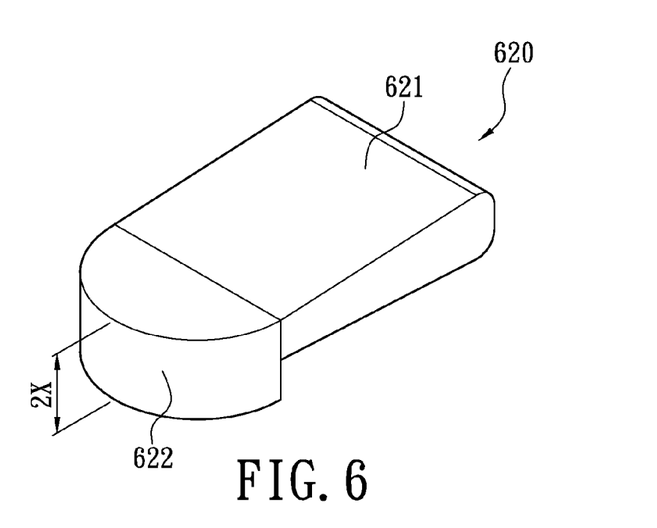
FIG. 6 illustrates an isometric view of a plank unit 120 in accordance with an alternative embodiment of the instant disclosure.

In the instant embodiment, the support surface (e.g. 122a/122b) can be arranged to resemble a triangular shape or a circular segment, as shown in FIG. 4 and FIG. 6, respectively. Specifically, FIG. 6 presents another embodiment of the plank unit 620 in accordance with the instant disclosure. The plank unit 620 has a support portion 622 and a tenon portion 621 extending therefrom, where the support surfaces of the support portion 622 have shapes of a circular segment. Similar to the previous embodiment, the thickness (height) of the support portion 622 is 2x. Of course, the practical design of the plank unit 622 does not need to be restricted to the limitations recited in the instant example. Both embodiments shown in FIG. 4 and FIG. 6 utilize a front-narrow support surface design, which provides easier unloading of a test object supported thereon. However, the specific design arrangement need to be restricted to the example provided herein. Please refer specifically to FIGS. 5 and 6 for a clearer illustration of the vertically unsymmetrical arrangement of the support portion (122, 622). Specifically, in the above exemplary embodiments, the upper support surface 122a is substantially flush with the upper surface of the tenon portion 121, while the lower support surface 122b is positioned below the lower surface of the tenon portion 121 (using the orientation provided by the figures). Preferably, the supporting portion 122 has a thickness substantially equal to the sum of the width of the mortise 111 and the thickness of the dividing member 113. This biased height arrangement not only enables the plank unit 120 to provide higher degree of height adjustment variation (through selection between the two different insertion orientations), it also allows two plank units 120 arranged in a vertically adjacent configuration to structurally abut against each other, thereby enhancing structural integrity of the support portion and increasing the load carrying capacity thereof.

Figure 7:
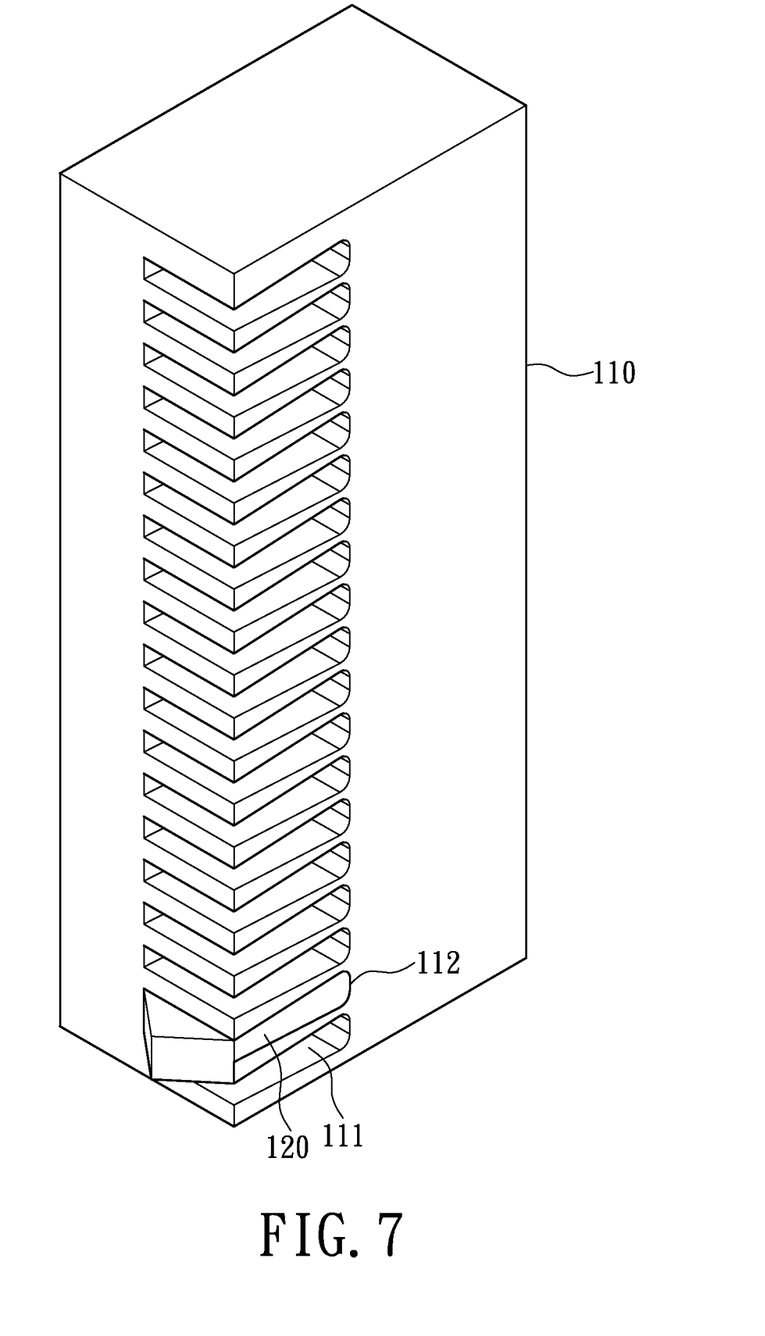
FIG. 7 illustrates an isometric view of a height adjustable support unit 100 in accordance with the first embodiment of the instant disclosure with the plank unit 120 inserted in place.

Please refer to FIG. 7, which shows an isometric view of a height adjustable support apparatus 100 in accordance with the first embodiment of the instant disclosure, where the plank unit 120 is properly inserted into mortise 112 of the frame unit 110. Because of the unsymmetrical/biased height configuration of the plank unit 120, the insertion orientation of the plank unit 120 provides different support surface altitude variations. In this particular instance as shown in FIG. 7, the thickness of the support portion 122 is 2x, the flush upper support surface 122a is upwardly arranged, while the lower support surface 122b, which has a position below the tenon portion 121, is arranged facing downward. When the plank unit 120 is inserted into the mortise 112 in the upright orientation, the upward-facing upper support surface 122a is substantially flush with the upper boundary of the second side opening 112b, while the downward-facing lower support surface 122a is substantially flush with the upper boundary of the second side opening 111b. Conversely, when the plank unit 120 is inserted into the mortise 112 in the reversed orientation, the upper support surface 122a becomes facing downward instead, and is substantially flush with the lower boundary of the second side opening 122b. Meanwhile, the lower support surface 122b, which is facing upward in this arrangement, is substantially flush with the lower boundary of an upward-neighboring mortise (i.e. the second side opening of the mortise above mortise 112).

Figure 8:
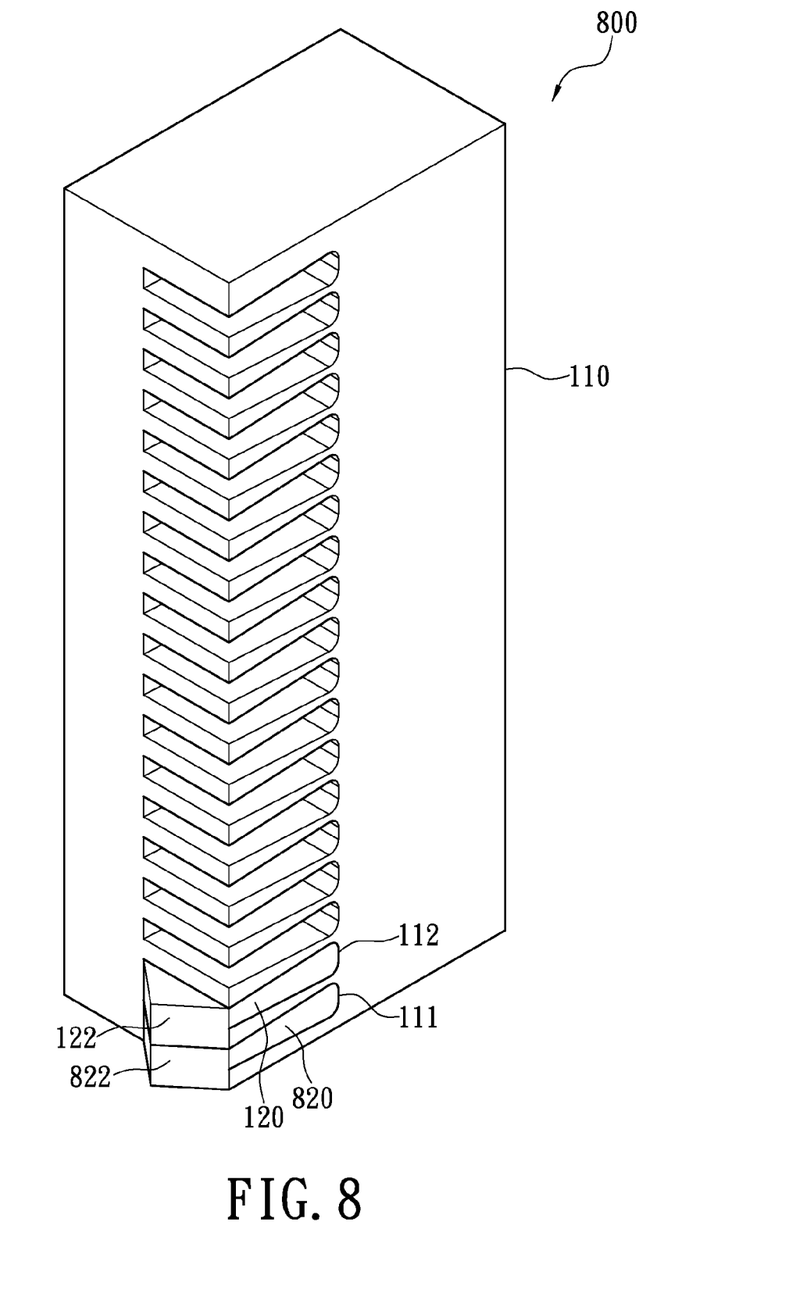
FIG. 8 illustrates a frame unit having two plank units inserted in accordance with the first embodiment of the instant disclosure.

Please refer to FIG. 8, which shows an exemplary frame unit 800 having two plank units (120, 820) inserted vertically adjacent to each other in accordance with the first embodiment of the instant disclosure. As mentioned above, the frame unit 110 can simultaneously receive more than one plank units 120 in a vertically abutting arrangement to provide higher load carrying capacity. Specifically, as shown in FIG. 8, the frame unit 110 concurrently receives two plank units 120 and 820 in its mortises 111 and 112, respectively, in a vertically adjacent manner. The support portion 822 of plank unit 820 abuts against the support portion 122 of plank 120 from below, thereby providing additional structural support. Likewise, multiple plank units can be adjacently arranged in the abovementioned manner to yield further increase in load carrying capacity.

Accordingly, the instant exemplary embodiment utilizes the flip-insertion of the plank unit 120 and the upright/reversed orientations of the frame unit 110 to provide a greater degree of drop-test altitude selection. Moreover, the unsymmetrical/biased height configuration of the plank unit (e.g. 120/820) allows the establishment of inter-unit support between vertically neighboring units, which provides greater structural integrity that leads to higher load carrying capacity.

[Second Embodiment]

Figure 9:
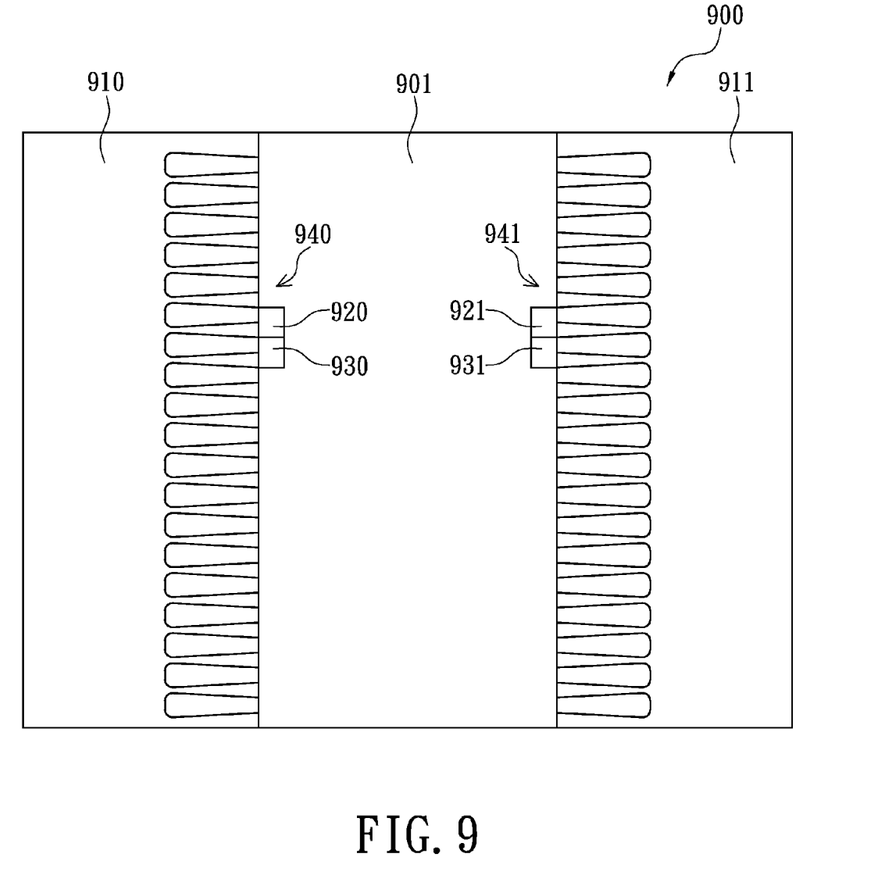
FIG. 9 illustrates a height adjustable support apparatus in accordance with a second embedment of the instant disclosure.

Please refer to FIG. 9, which illustrates a height adjustable support apparatus in accordance with a second embedment of the instant disclosure. The height adjustable support apparatus 900 comprises a main body 901 and a pair of symmetrically mirroring support frame structures 910, 911 respectively arranged on the opposite lateral sides of the main body 901. Each of the support frame structures 910, 911 shares similar structural design with the frame unit 110 of the first embodiment (which are clearly recognizable from FIG. 9), thus, the details of such identical structural features will not be repeatedly discussed. Similar to the structural feature of the frame unit 110 from the previous embodiment, the each of the support frame structures 910 and 911 has a plurality of mortises correspondingly arranged with substantially equal separation there-between at the adjoining edge of their respective lateral surfaces, respectively forming comb-like structures 940 and 941 (when viewing from a side angle, as shown in FIG. 9). Similar to the previous embodiment, the comb-like mortise structures are configured to receive the tenon of the plank units 920/921/930/931. Referring specifically to FIG. 9, the mortises/slots of the support frame structure 910 on the left are correspondingly configured to match with the height of the mortises/slots of the support frame structure 911 on the right in a substantially symmetrically mirroring arrangement for providing balanced support to a test object. Also similar to the previous embodiment, more than one plank unit (e.g. 921 and 931) can be vertically abuttingly arranged to provide increased load carrying capacity.

The height adjustable support apparatus 100 provides an ideal mean for conducting single side drop test for notebook computers or other comparable electronic products, while the symmetrically configured support apparatus 900 provides an ideal mean for the conduction of leveled drop test. In addition, the above disclosed support apparatus 100/900 may be adapted for other conventional purposes, such as being utilized as a bookshelf or a storage rack.

In conclusion, the instant disclosure provides a height adjustable support apparatus, where the height of the support surface thereof can be easily adjusted and securely configured to support a wide range of weight loading, thereby providing higher degree of operating convenience and practicality, and eliminating the redundant need for having multiple drop-test carriers of different heights.

While the invention has been disclosed with respect to a limited number of embodiments, numerous modifications and variations will be appreciated by those skilled in the art. It is intended, therefore, that the following claims cover all such modifications and variations that may fall within the true spirit and scope of the invention.

What is claimed is:

1. A support apparatus, comprising:
   a frame unit having adjoining first and second lateral surfaces, wherein a plurality of mortises are vertically incrementally arranged with substantially equal separation at the adjoining edge of the first and the second lateral surfaces between a top frame surface and a bottom frame surface,
   wherein each mortise constitutes a first side opening accessible from the first lateral surface and a second side opening accessible from the second lateral surface, the first side openings define a comb-like structure on the first lateral surface, wherein the first side opening of the mortise is tapered with a first end thereof proximate the second lateral surface being narrower than a second end thereof opposite to the first end; and
   a first plank unit having a first support portion and a first tenon extending from the first support portion, the first tenon being configured to be insertable into one of the plurality of mortises through the first side opening, the first support portion being configured to protrude from the second side opening;
   wherein the thickness of the first support portion is greater than the width of the second side opening;
   wherein upon insertion into a first mortise of the plurality of mortises, an upper support surface of the first support portion is substantially flush with an upper boundary of the first mortise, while a bottom support surface of the first support portion is substantially flush with an upper boundary of a second mortise immediately below the first mortise.

2. The support apparatus of claim 1, wherein the plurality of mortises are configured to be vertically symmetrical, wherein the tenon of the first plank unit is correspondingly shaped to allow structural adaptation into the mortises.

3. The support apparatus of claim 1, wherein the second side openings of the mortises on the second lateral surface have substantially identical opening widths, and wherein the separation distance between each pair of adjacent second side openings substantially equals to the opening width.

4. The support apparatus of claim 1, wherein the support surfaces of the first support portion are arranged substantially in a triangular shape or the shape of a circular segment.

5. The support apparatus of claim 1, wherein the width of each of the mortises is defined by the width of the second side openings of the mortises on the second lateral surface and is substantially identical, wherein the thickness of the first support portion of the first plank unit is twice the width of the second side opening of the mortise.

6. The support apparatus of claim 1, further comprising:
   a second plank unit having a second support portion and a second tenon extending from the second support portion,
     the second tenon being configured to be insertable into one of the plurality of mortises through the first side opening,
     the second support portion being configured to protrude from the second side opening,
   wherein when the first and the second plank units are arranged in a vertically adjacent configuration, an upper support surface of the second support portion abuts against the bottom support surface of the first support portion from below.

7. A support apparatus, comprising:
a main body;
a first support structure and a second support structure respectively arranged on the opposite lateral sides of the main body, wherein the first support structure comprises:
  a first frame body having adjoining first and second lateral surfaces, wherein a plurality of mortises are vertically incrementally arranged with substantially equal separation at the adjoining edge of the first and the second lateral surfaces between a top frame surface and a bottom frame surface thereof,
    wherein each mortise constitutes a first side opening accessible from the first lateral surface and a second side opening accessible from the second lateral surface, the first side openings define a comb-like structure on the first lateral surface;
    wherein the first side opening of the mortise is tapered with a first end thereof proximate the second lateral surface being narrower than a second end thereof opposite to the first end; and
  a first plank unit having a first support portion and a first tenon extending from the first support portion, the first tenon being configured to be insertable into one of the plurality of mortises through the first side opening, the first support portion being configured to protrude from the second side opening;
    wherein the thickness of the first support portion is greater than the width of the second side opening;
    wherein upon insertion into a first mortise of the plurality of mortises, an upper support surface of the first support portion is substantially flush with an upper boundary of the first mortise, while a bottom support surface of the first support portion is substantially flush with an upper boundary of a second mortise immediately below the first mortise.

8. The support apparatus of claim 7, wherein the plurality of mortises are configured to be vertically symmetrical, wherein the tenon of the first plank unit is correspondingly shaped to allow structural adaptation into the mortises.

9. The support apparatus of claim 7, wherein the second side openings of the mortises on the second lateral surface have substantially identical opening widths, and wherein the separation distance between each pair of adjacent second side openings substantially equals to the opening width.

10. The support apparatus of claim 7, wherein the support surfaces of the first support portion arranged substantially in a triangular shape or the shape of a circular segment.

11. The support apparatus of claim 7, wherein the width of each of the mortises is defined by the width of the second side openings of the mortises on the second lateral surface and is substantially identical, wherein the thickness of the first support portion of the first plank unit is twice the width of the second side opening of the mortise.

12. The support apparatus of claim 7, further comprising:
a second plank unit having a second support portion and a second tenon extending from the second support portion,
  the second tenon being configured to be insertable into one of the plurality of mortises through the first side opening,
  the second support portion being configured to protrude from the second side opening,
wherein when the first and the second plank units are arranged in a vertically adjacent configuration, an upper support surface of the second support portion abuts against the bottom support surface of the first support portion from below.

13. The support apparatus of claim 7, further comprising:
a second frame body having a plurality of mortises correspondingly symmetrically mirroring the mortises of the first support structure and defining a second comb-like structure, and
a third plank unit having a third support portion and a third tenon extending from the third support portion, the third tenon being configured to be insertable into one of the second frame body through the second comb-like structure, the third support portion being configured to protrude from the second side opening.

* * * * *